(12) United States Patent
Wong

(10) Patent No.: US 8,158,946 B2
(45) Date of Patent: *Apr. 17, 2012

(54) INTRINSICALLY SAFE IMPROVED SENSITIVITY NDIR GAS SENSOR IN A CAN

(75) Inventor: Jacob Y Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/210,255

(22) Filed: Aug. 15, 2011

(65) Prior Publication Data

US 2012/0049071 A1    Mar. 1, 2012

Related U.S. Application Data

(63) Continuation-in-part of application No. 12/868,628, filed on Aug. 25, 2010, now Pat. No. 8,003,945.

(51) Int. Cl.
*G01J 5/02* (2006.01)
(52) U.S. Cl. .................................................. 250/343
(58) Field of Classification Search .................. 250/343
See application file for complete search history.

(56) References Cited

U.S. PATENT DOCUMENTS

| 6,991,987 B1 * | 1/2006 | Guo et al. ..................... 438/264 |
| 7,063,667 B1 * | 6/2006 | Ben-Oren et al. ............. 600/532 |
| 8,003,945 B1 * | 8/2011 | Wong .............................. 250/343 |

* cited by examiner

*Primary Examiner* — Christine Sung
(74) *Attorney, Agent, or Firm* — Roy L Anderson; Wagner, Anderson & Bright, P.C.

(57) ABSTRACT

An NDIR gas sensor takes advantage of a conventional packaging embodiment commonly used to house detectors of all kinds comprising a can, header and a dish sample chamber all welded together to form a single detector unit. The can forms the top, a hollowed out header body forms the middle and a custom dish sample chamber forms the bottom of a completely functioning NDIR gas sensor. Whereas the header body not only accommodates all the optoelectronic and optical parts on its top surface providing the required signal processing functions for the gas sensor, part of its body is excavated below to accommodate a custom dish sample chamber in communication with the gas outside whose concentration level is to be measured. A lens and windows are also fabricated on the top part of this header body so that infrared radiation can enter the dish sample chamber below and then be redirected back above for signal processing. To achieve this optical feat, strategic reflecting surfaces are impregnated on the top of the can housing so as to direct infrared radiation to the dish sample chamber below through a lens and then redirect the radiation above via another window for subsequent signal detection and processing.

20 Claims, 6 Drawing Sheets

INTRINSICALLY SAFE IMPROVED SENSITIVITY NDIR GAS SENSOR IN A CAN

CROSS-REFERENCE TO RELATED APPLICATIONS

This application claims priority from and is a continuation-in-part application of U.S. Ser. No. 12/868,628, filed Aug. 25, 2010, the disclosure of which is specifically incorporated herein by reference.

FIELD OF THE INVENTION

The present application is in the field of gas analysis, and specifically relates to apparatus using a Non-Dispersive Infrared (NDIR) gas analysis technique to determine the concentration of a gas of interest that is present in a chamber by sensing the absorption of infrared radiation passing through the gas.

BACKGROUND OF THE INVENTION

Coal and crude oil are two of the most important fossil fuels in use in the world today to satisfy our energy needs. Particularly in countries like the U.S. and China, where there are enormous deposits of coal in their land, mining of coal is even more important, if not indispensable. No doubt the acquisition of other energy sources such as gas and crude oil also involves dangerous everyday operations, but coal mining has to take the top spot as far as the number of workers that perish every year is concerned. It is believed that explosions in mines alone inside China have claimed more than half a million lives during the past decade. Although the number of miners killed elsewhere in the world during mining operations is far less than those reported inside China, the number still runs into many thousands every year.

The cause of explosions inside mines has become fairly well understood over the years. The presence of methane gas ($CH_4$) pockets is known to exist and scatter unpredictably among rocks containing coal deposits. Methane gas is odorless and the lower explosion limit (LEL) of methane gas is around 5.0 volume percent in air containing ~21 vol. % of oxygen. It is generally believed that underground mine explosions are caused by miners accidentally and unknowingly hitting a methane gas ($CH_4$) pocket in the mine while they are crushing and churning rocks by hand or with massive machines to get to coal deposits in tunnels. Without knowing the existence of an explosive air mixture in their work area so as to stop working immediately, the miners' operation continues to generate sparks that ultimately lead to the unfortunate explosion. Such underground mine explosions could surely be prevented if only the miners knew that immediate ambient air they are breathing has reached a lower explosion limit (LEL) for methane gas and they have to immediately stop operating their machines or rock churning by hand in order not to generate any sparks that could set off an explosion. Although methane gas sensors can detect LEL concentration levels for methane gas when such sensors are stationed at adequate distances inside mine tunnels, it is not always the case that such a sensor is in the immediate vicinity of the space where the miners are doing the heavy work. Without the presence of such a methane sensor in the space to warn the miners of such a dangerous situation where they work, underground mine explosions will inevitably occur from time to time causing the lives of many miners every year.

It has long been understood and believed that in order to eliminate the danger of underground mine explosions caused by the methane gas, one has to fulfill two important monitoring functions for mines. The first is an integrated communication and tracking system designed specifically for use in underground mines. Such a system not only is able to continuously track the exact whereabouts of the miners underground, it is also capable of monitoring in real time the outputs of all the installed gas sensors stationed inside the mine in order to be able to assess at all times any dangerous levels of gas built-ups at locations that might trigger an explosion. Over the past decade a small number of such integrated communication and tracking systems have become available. Within the last couple of years, some of them have even been installed for testing in a small number of mines around the world. For tracking individual miners working underground, an effective way is to install wireless location sensors in the helmets of miners that communicate directly with the central system above ground. The whereabouts of individual miners underground can now be continuously tracked and notified if necessary to evacuate from specific locations in case of potential danger.

But while the availability of such an integrated communication and tracking system for mines is a necessary requirement for eliminating the danger of underground mine explosions, it is not sufficient by itself to eliminate such danger. The reason is relatively straightforward. Although an expertly functioning communication and tracking system can pin point the location of a potentially explosive environment via monitoring of a fixed system of methane sensors strategically scattered throughout the tunnels of the mine, it cannot follow the exact locale of a crew of miners underground at work. If the crew cannot sense the danger of an explosive environment they find themselves in while they are working, an explosion can still occur. However, if the crew is provided with means to accurately and reliably detect the dangerous level of methane in their midst, they can immediately take action to avoid the possibility of explosions and evacuate the site. Meanwhile the central system can also take note of the dangerous condition at this location and notify other miners nearby to evacuate until the environment is under control and is safe again.

The ability of an integrated communication and tracking system for mines to pin point the whereabouts of every miner working underground can be achieved via installation of a wireless location sensor in the helmet of each of these miners. Imagine that the helmet of every miner working underground is also equipped with a wireless and intrinsically safe methane sensor capable of accurately detecting a dangerous level of methane (like the LEL) in the vicinity of working miners; in this scenario, the second important monitoring function necessary and sufficient to eliminate the danger of underground mine explosions mentioned will be fulfilled.

However, despite a long felt need for increased mine safety, and the imperative of saving miner's lives, an integrated communication and tracking system for mines does not yet exist, at least not with a methane sensor that can adequately function in such a system. This invention fulfills this long felt need by providing an intrinsically safe methane sensor that satisfies the criteria necessary for a methane sensor to be effectively and economically integrated into a communication and tracking system for mines.

SUMMARY OF THE INVENTION

The present invention is generally directed to a NDIR gas sensor that is housed within a mechanical housing made up of a can and a header housing. The header housing has a bottom header containing a radiation path length created through use of two mirrors and multiple reflecting surfaces so that the path length is substantially greater than the distance between the mirrors. The header housing also has a top surface with a pair of windows formed in it and a signal detector, a reference detector, a MEMS source and a signal processor mounted to it. The can has inner reflective surfaces and the reference detector and the signal detector are affixed to the top surface so that the inner reflective surfaces of the can and the path length of bottom header create a signal channel path length detected by the signal detector that is greater than a reference channel path length detected by the reference detector and an absorption bias between the signal and reference outputs can be used to determine a gas concentration in the sample chamber. Both the signal detector and the reference detector have an identical narrow band pass filter with the same Center Wavelength ("CWL"), Full Width Half Maximum (FWHM) and transmittance efficiency at the CWL.

In a first, separate group of aspects of the present invention, the header is sealed to the can so as to create a hermetically sealed environment containing the top surface and the NDIR gas sensor is used to detect methane.

In a second, separate group of aspects of the present invention, the header is comprised of a metal and the microprocessor is a wire-bondable Central Processing Unit ("CPU") die which can include a temperature sensor. In addition, a voltage regulator and an electrical heater die (for regulating the temperature of the header housing) can be mounted to the top surface.

In a third, separate group of aspects of the present invention, each of the reference detector and the signal detector are comprised of a thermopile detector with the identical narrow band pass filter mounted on its top and communicable with an Application Specific Integrated Circuit ("ASIC") such that infrared radiation received by the thermopile detector after passing through the identical narrow band pass filter is converted into a digital signal ready to be transmitted to the microprocessor.

Accordingly, it is a primary object of the present invention to advance a NDIR gas sensor that implements an Absorption Biased methodology for NDIR gas sensors in an intrinsically safe design with an increased Signal Channel path length.

These and further objectives and advantages will be apparent to those skilled in the art in connection with the drawings and the detailed description of the invention set forth below.

DETAILED DESCRIPTION OF THE INVENTION

Figure 1:
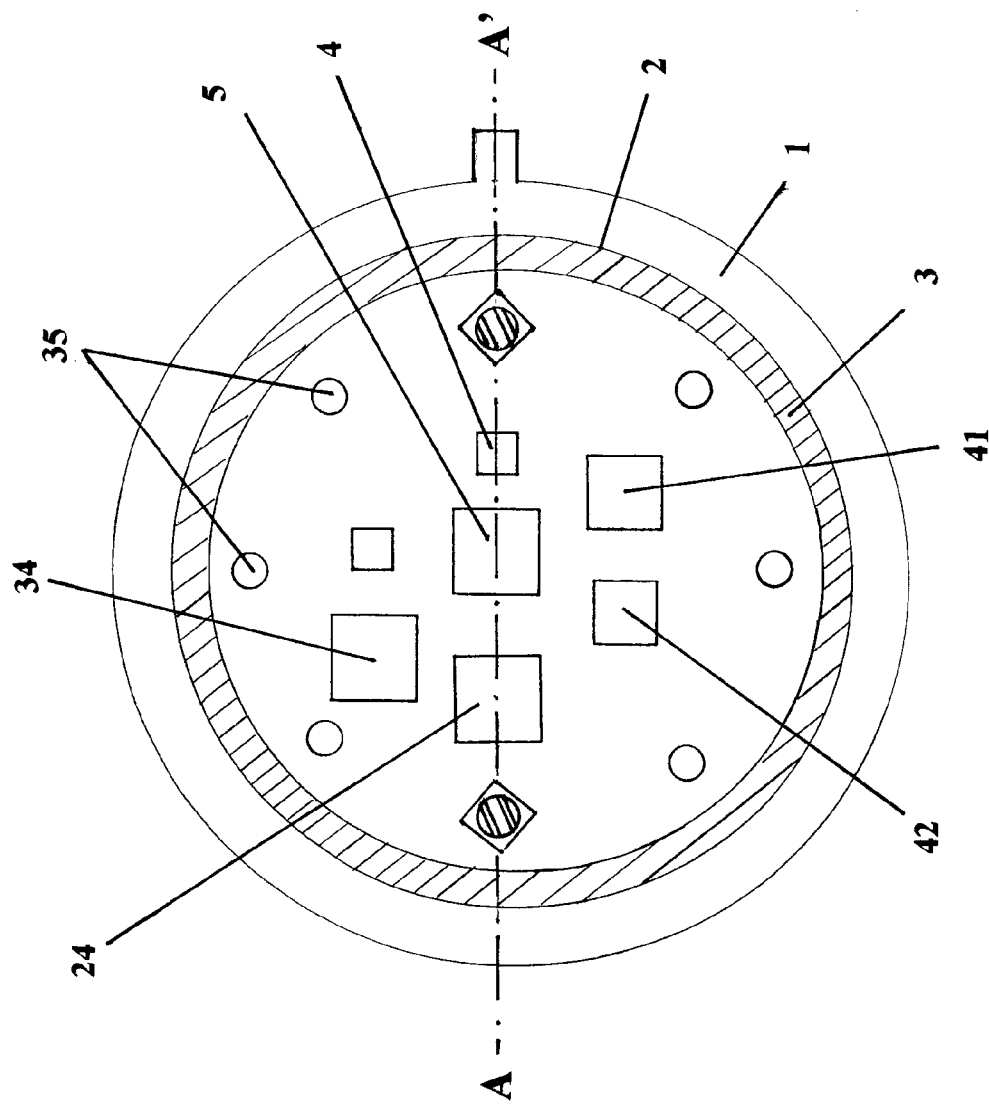
FIG. 1 depicts the placement of all the optoelectronic components on top of a detector header forming the top two-third section of a sensor housing according to the present invention.

The present invention proposes a solution to the problem of methane sensors in an underground mining communication and tracking system by using a methane sensor which is in actuality a methane fuse capable of sounding a signal or alarm when a dangerous and predetermined concentration level of methane is exceeded. Since the LEL of methane in regular air containing approximately 21.0 volume percent of oxygen is 5.0 volume percent or 50,000 ppm, the alarm level for a methane fuse can be safely set at 1.0 volume percent or 10,000 ppm.

In order for such a methane fuse to be useful and effective it should satisfy many stringent performance requirements, all of which are met by a methane fuse according to the present invention. First and foremost, it must be intrinsically safe to be able to be operated inside a mine without itself causing any potential explosions. Second, its output must stay accurate over time and if there should be an unavoidable output drift over time, it must be able to be checked and if necessary be recalibrated back to accuracy effortlessly and in a matter of 1-2 minutes or less. That way it becomes possible for a miner to check this methane fuse every time the miner re-enters the mine for work underground. Third, its methane measurement sensitivity and accuracy must be better than +/−250 ppm with a response time (0-90%) of 10 seconds or less and its output correctable for temperature changes in order to be able to forewarn miners with time to spare before a LEL level of methane is reached. Fourth, this methane fuse must be small in size so it can easily be installed in a miner's helmet. Fifth, it must be rugged, completely solid state and shock resistant. Sixth, its output must be interference free from other common gases present underground so as not to cause any costly false alarms. Seventh, it must consume only a very small amount of power so that its continuous operation can last for at least a miner's work shift underground while sharing the same battery powering the lamp in his helmet. Eighth, its function must be compatible with the integrated communication and tracking system for the mine so that its alarm can also be heeded at the central station in addition to being heeded by the miner wearing it in the miner's helmet. Last but not least, it must be very low cost so that it can be installed in every miner's helmet.

Recently the present inventor advanced in U.S. patent application Ser. No. 12/859,749 filed Aug. 19, 2010, the disclosure of which is specifically incorporated herein by reference, a new NDIR gas sensing methodology which renders to first order the output of an NDIR gas sensor designed using this methodology virtually drift-free over time without the need for any sensor output correction software or periodic recalibration. The present inventor has also recently advanced in U.S. patent application Ser. No. 12/868,628 filed Aug. 25, 2010 a novel design incorporating the present inventor's teaching advanced in U.S. patent application Ser. No. 12/859,749 filed Aug. 19, 2010 for an intrinsically safe NDIR gas sensor in a can with has virtually no output drifts over time. The design of an NDIR gas sensor incorporating the above two teachings advanced by the present inventor, namely U.S. Ser. Nos. 12/859,749 and 12/868,628, would have met all the stringent performance requirements for a methane fuse discussed above except for the sensor sensitivity requirement. The reason is that the sample chamber path length for an intrinsically safe NDIR gas sensor designed as a can is too short because of its small size to achieve the kind of sensitivity requirement for the detection of methane gas. For an NDIR gas sensor designed as an intrinsically safe can to be used as a methane fuse in a mine with a sensitivity of at least +/−250 ppm of methane it must have a much longer path length.

The present invention sets forth the configurational housing for an improved sensitivity innovative sensor combining interactively all the needed optical, mechanical and electronic components together into a functioning NDIR gas sensor occupying typically less than a few cubic centimeters of physical space.

My Absorption Biased methodology for NDIR gas sensors, disclosed in Ser. No. 12/859,749, follows the general design principle of a dual-channel implementation, namely a signal and a reference channel working in synchronism as a ratio for signal processing. In this disclosure it is taught that both the signal and the reference detectors for the two channels are to be equipped with an identical narrow band pass spectral filter having the same Center Wavelength (CWL), Full Width Half Maximum (FWHM) and transmittance efficiency at CWL. Furthermore, both detectors receive infrared radiation from one single source. It is further taught that in order for the methodology to work properly, the two separate detectors, with their individual detector element and identical spectral filter, must share a common thermal platform. This is because the individual spectral filters are extremely temperature sensitive and in order for the methodology to work as designed, these components must track in temperature at all times.

The present invention advances an innovative sensor housing for implementing the so-called Absorption Biased methodology for NDIR gas sensors referred to above and interactively combining all the needed opto-electronic, opto-mechanical and electronic components together into a functioning gas sensor network occupying a small physical space. A modified mechanical housing unit, used commonly for the packaging of thermopile detectors, comprising a metallic header ~0.500" in diameter and ~0.150" thick but with a portion of it hollowed out to accommodate snugly a special dish-like sample chamber at its bottom. A metal can typically 0.250" tall that can be welded onto the header for creating a hermetically sealed environment is used to accommodate all the needed opto-electronic, opto-mechanical and electronic components for constituting a fully functional NDIR gas sensor.

In order to achieve this, all the needed optoelectronic, opto-mechanical and electronic components must be specially designed and fabricated, not only to fit the overall sensor housing for assembly, but also to be able to interact functionally together as a gas sensor unit. There are three such optoelectronic components, namely two Integrated Detector Filter ASIC (IDFA) modules and a MEMS Infrared Source (MIS) module. The IDFA module comprises a thermopile detector with a selectable thin film narrow bandpass filter mounted on top communicable with an Application Specific Integrated Circuit (ASIC) such that infrared radiation received by the detector after passing through the narrow bandpass filter is converted into a digital signal ready to be transmitted to a CPU die for signal processing. The MIS module is simply an infrared MEMS source such that it emits radiation when power is applied to it.

There are also three electronic components that have to be specially designed for the present invention. The first one is a wire-bondable CPU die which can digitally receive, process and output information wired to its input and output pads. Included in this CPU die is also a temperature sensor. The second custom component is a wire-bondable electrical heater die which is used to supply needed heat to temperature regulate the sensor housing if required. The third custom component is a wire-bondable voltage regulator die which translates available input voltage levels to those that are required to power the optoelectronic components (see above), the CPU die and the heater die.

Finally there are three opto-mechanical components that have to be specially designed for the present invention. The first two are the can and the modified header of a detector housing typically used to package infrared detectors such as a thermopile. The can is designed to function as mirrors comprising various reflecting surfaces to direct and re-direct radiation above and below the header through openings in the header body covered by optical windows or lenses. The bottom of the header is hollowed out to accommodate snugly a custom designed dish which is the third opto-mechanical component. This custom designed dish has reflecting surfaces strategically fabricated at its side wall to redirect radiation coming down from the can side of the housing after being bent 90° to be parallel to the header surface. This radiation is made to bounce back and forth orderly in this dish before it is being redirected upwards back to the can side of the housing above. In this way the dish serves as a sample chamber for the sensor with adjustable path length which can be rendered as long as is required. This custom dish sample chamber which fits snugly onto the bottom of the hollowed-out header is also designed to communicate with the outside air through openings at its side. Covering these openings are a thin layer of polyethylene functioning as air filters in the form of a rubber-band-like ring encircling the header which has openings lining up exactly with those at the side of the custom dish.

The present invention describes how these specially designed components described above are to be assembled together into a mechanical embodiment such as a conventional detector housing and performs functionally as a superb NDIR gas sensor. The present invention will now be described in even greater detail by reference to one preferred embodiment that is illustrated in the Figures. Although the Figures are described in greater detail below, the following is a glossary of the elements identified in the Figures.

Figure 2:
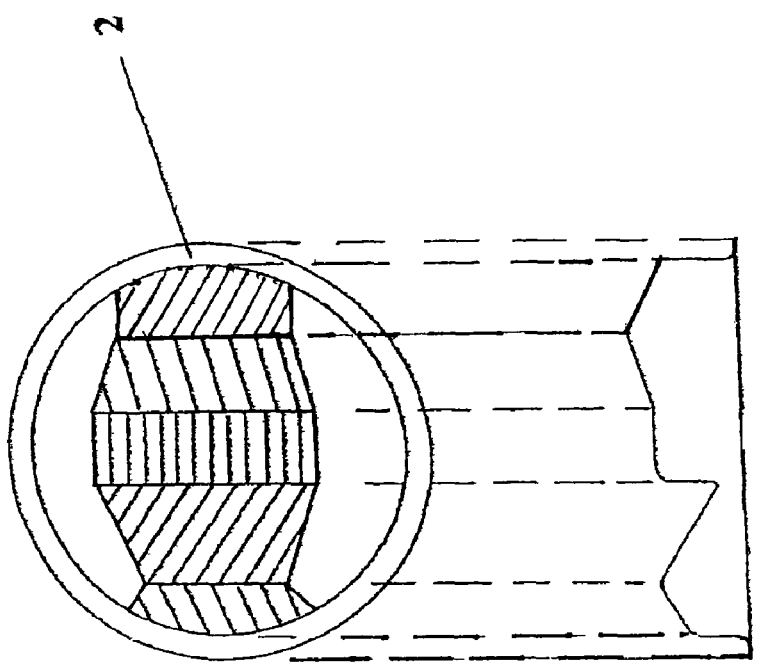
FIG. 2 depicts schematically the detector can of FIG. 1 with its custom reflecting surfaces impregnated inside its top constituting the top one-third section of the sensor housing of the present invention.
Figure 3:
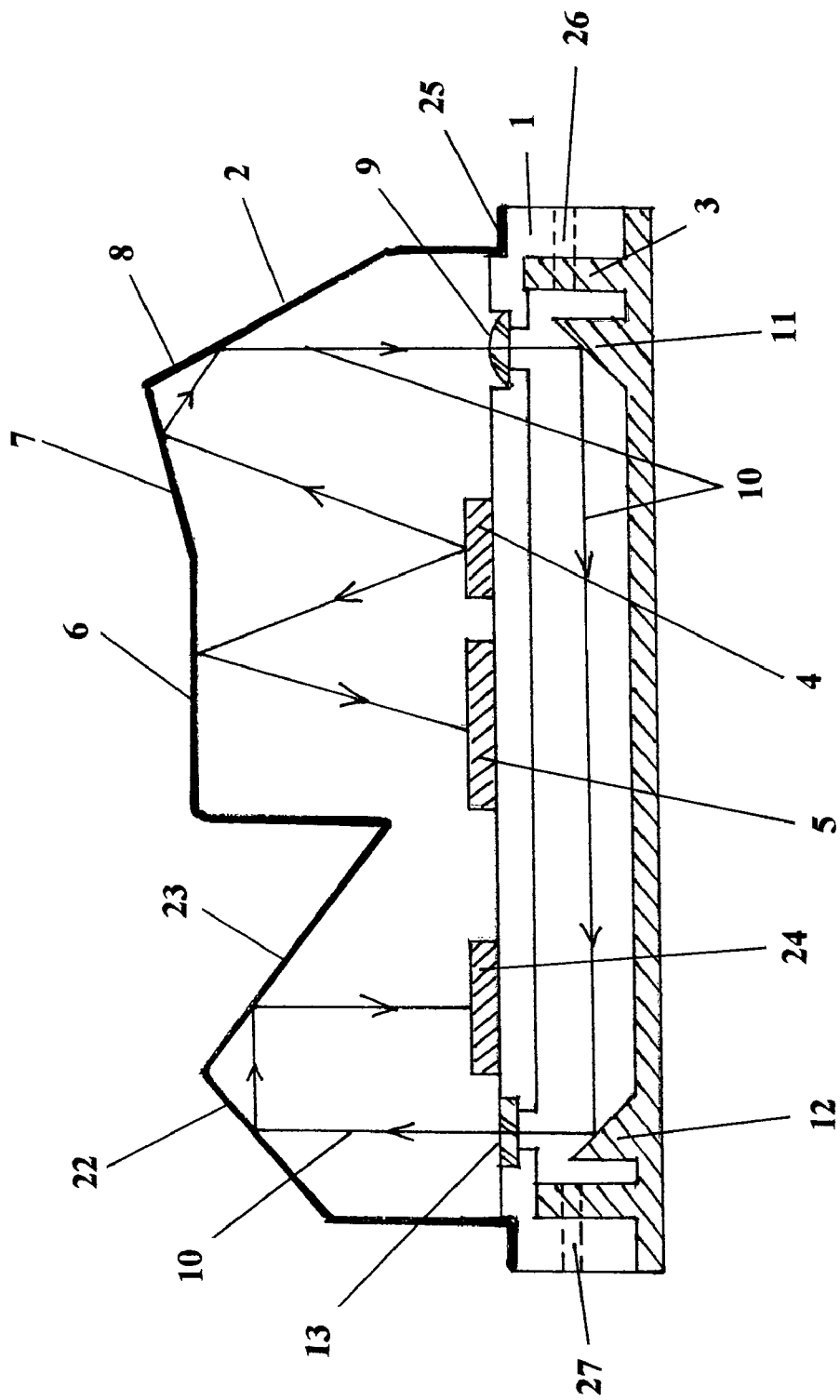
FIG. 3 depicts a cross-sectional view of the sensor housing along AA' of FIG. 1 when the top can, the middle header and the bottom dish sample chamber of the sensor housing are welded together to form the entire body of a fully functional NDIR gas sensor.

1 detector header housing
2 detector can
3 custom dish sample chamber
4 MEMS module
5 detector module
6 reflecting surface (in the Reference channel)
7 reflecting surface
8 reflecting surface
9 lens
10 radiation
11 mirror
12 mirror
13 window
14 reflecting surface
15 reflecting surface
16 reflecting surface
17 reflecting surface
18 reflecting surface
19 center of mirror 11
20 center of mirror 12
22 reflecting surface (in the Signal channel)
23 reflecting surface (in the Signal channel)
24 detector module 25 welding joint
26 opening
27 opening
28 thermopile detector
29 narrow bandpass interference filter
30 Application Specific Integrated Circuit ("ASIC")
32 wire bondable pad
33 surface mountable pad
34 wire bondable CPU die
35 lead
36 platinum film
37 heater resistive structure
38 thin $Si_3N_a$ membrane
39 silicon substrate cavity structure
40 wire bondable pad
41 wire bondable voltage regulator die
42 heater die FIG. 1 shows the placement and arrangement of all the optoelectronic components on top of detector header housing 1 forming the middle section of the sensor assembly for the present invention. FIG. 2 shows schematically detector can 2 with its reflecting surfaces impregnated inside its top constituting the top third of the sensor assembly of the present invention. FIG. 3 depicts a cross-sectional view of the sensor assembly (along AA' of FIG. 1) of the present invention when the detector can 2 (see FIG. 2) and the custom dish sample chamber 3 are welded to the detector header 1 (see FIG. 1) forming the entire body of a fully functioning NDIR gas sensor.

With reference to FIG. 3, part of the infrared radiation emanating from MEMS module 4 (see also FIG. 1) is reflected onto detector module 5 via reflecting surface 6 constituting the Reference channel of the presently invented NDIR gas sensor fuse. Another part of the infrared radiation emanating from MEMS module 4 enters perpendicularly via reflecting surfaces 7 and 8 through lens 9 (see FIG. 3) into the custom dish sample chamber 3 constituting the Signal channel of the presently invented NDIR gas sensor fuse. The function of lens 9 is to render the radiation beam entering custom dish sample chamber 3 relatively or substantially collimated. The radiation 10 entering dish sample chamber 3 is bent 90° by mirror 11 integral with dish sample chamber 3 so that radiation 10 is now propagating parallel to the top surface of the header. After bouncing around dish sample chamber 3 a designed number of times (see later), radiation 10 exits dish sample chamber 3 perpendicularly via mirror 12 and window 13 back into the space above the detector header 1.

Figure 4:
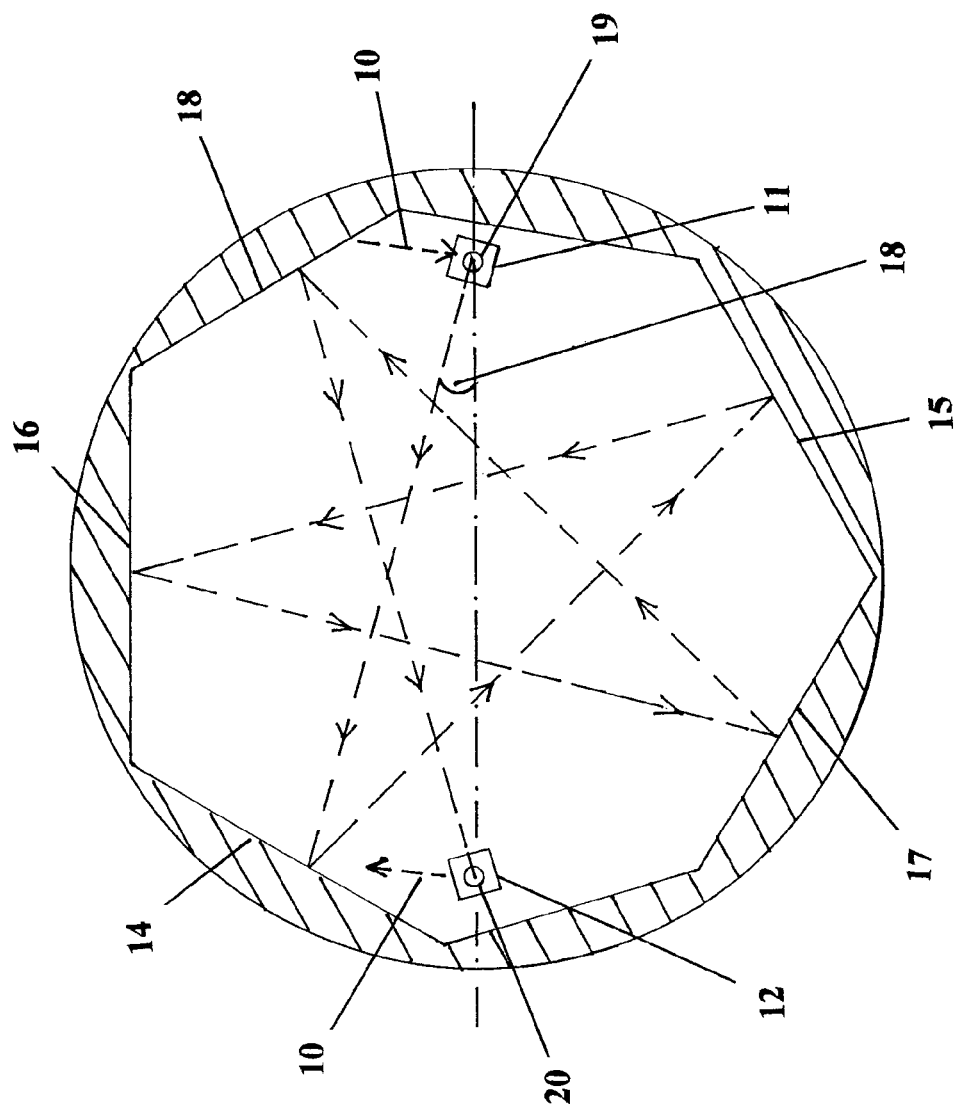
FIG. 4 depicts the bottom of a custom dish sample chamber according to a preferred embodiment of the present invention showing the orderly multiple bouncing of the radiation in order to achieve a much longer path length for the sensor.

FIG. 4 shows a bottom view of custom dish sample chamber 3. As shown in FIG. 4, radiation 10 entering dish sample chamber 3 perpendicular to it is being bent 90° by mirror 11 towards reflecting surface 14. Radiation 10 is now rendered parallel to the bottom of dish sample chamber 3. After respectively bouncing off reflecting surfaces 14 through 18, radiation 10 is bent 90° by mirror 12 towards window 13 and re-enters the space above header surface 1. The custom dish sample chamber 3 as shown in FIG. 4 is specially designed with mirrors 11 and 12 oriented by an angle 18 equal to 15° with respect to the axis adjoining their respective centers 19 and 20. This particular design yields an effective sample chamber path length roughly six times the diameter of the header housing. Since the diameter of the header housing is roughly 0.5", the effective path length for such a dish sample chamber is ~3.0" which is sufficient to achieve a detection sensitivity of +/−250 ppm for methane gas. Thus, one can configure the number of reflecting surfaces to achieve a desired path length that is substantially greater than what could be achieved without reliance upon multiple reflections off of multiple reflecting surfaces, as is shown in FIG. 4, depending upon the path length needed for a given NDIR sensor application.

Emerging radiation 10 (see FIG. 3) is then directed by reflection surfaces 22 and 23 of detector can 2 onto detector module 24. The formation of the Reference and Signal channels by the optoelectronic and optomechanical components of the present invention follows the teaching of the Absorption Biased methodology for NDIR gas sensors as disclosed in U.S. application Ser. No. 12/759,603 by the present inventor.

As can be seen from FIG. 3, since the space between detector can 2 and detector header 1 is sealed off from ambience by welding joint 25 (see FIG. 3), lens 9 and window 13 and is filled with 100% Nitrogen, the Reference channel does not feel any effect from ambient gas of interest to be detected (e.g. $CO_2$ or methane) present in the custom dish sample chamber 3 which is in communication with the outside ambient atmosphere through openings 26 and 27. On the other hand, infrared radiation emanated by MEMS module 4 for the Signal channel enters custom dish sample chamber 3 and bounces inside it a designed number of times in order to acquire a long path length prior to reaching detector module 24. Therefore the Signal channel will be sensitive to the presence of any gas of interest to be detected in the surrounding ambience which is in communication with the disk sample chamber 3 via openings 26 and 27.

Figure 5:
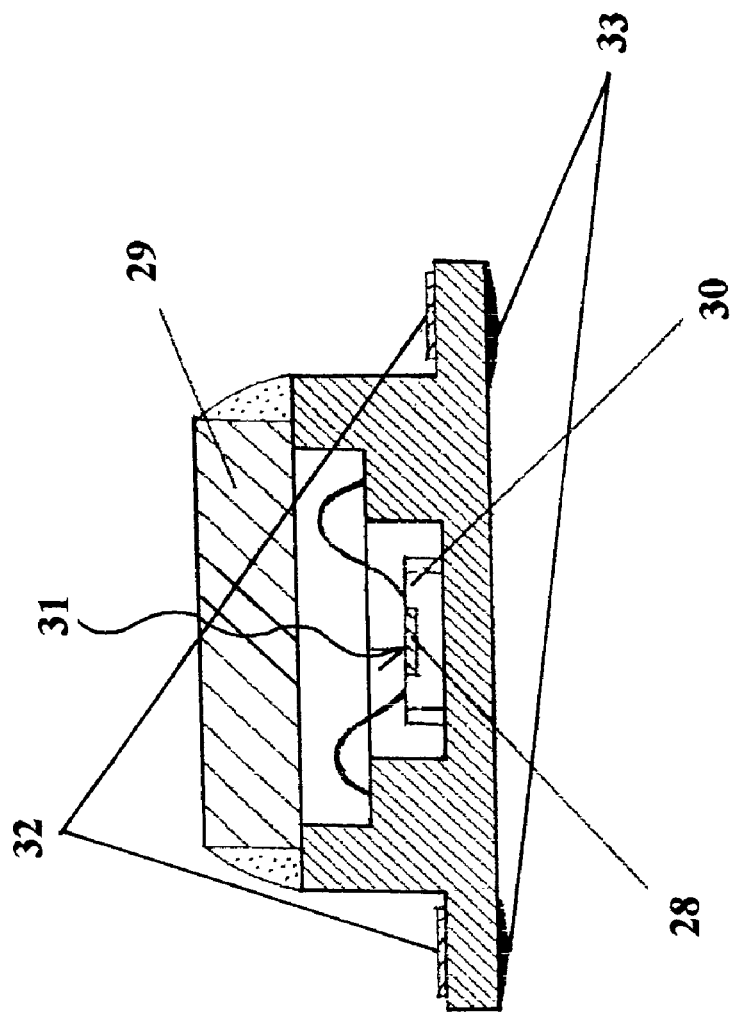
FIG. 5 depicts detail for the construct of the integrated detector filter ASIC module (IDFA) according to a preferred embodiment of the present invention which is a digital sensor device comprising a thermopile detector, a narrow band pass interference filter and an Application Specific Integrated Circuit (ASIC) electrically integrated together as a functioning unit.

The roles played by the optoelectronic components for performing the signal processing function of the presently invented NDIR gas sensor fuse will now be described. With reference to FIG. 1, Detector module 5 of the Reference channel and Detector module 24 of the Signal channel are identical devices. Such a detector module is in essence a digital sensor designed to be a surface mountable or wire bondable integrated circuit device comprising a thermopile detector 28, a narrow bandpass interference filter 29 fabricated on top and an Application Specific Integrated Circuit (ASIC) 30 all electrically interconnected as depicted in FIG. 5. With reference to FIG. 5, infrared radiation 31 incident on the thermopile detector 28 after passing through the filter 29 will be processed by ASIC 30 with the resulting signal available digitally for further processing elsewhere via wire bondable pads 32 or surface mountable pads 33. Thus both the Reference channel and Signal channel signals are processed respectively by Detector modules 5 and 24 with the resulting signals forwarded to a wire bondable CPU die 34 (see FIG. 1) for further processing. The final outputs of the NDIR gas sensor fuse are transmitted to the outside world from the CPU die 34 through 2 or more leads 35 of the detector header housing 1 (see FIG. 1).

Figure 6:
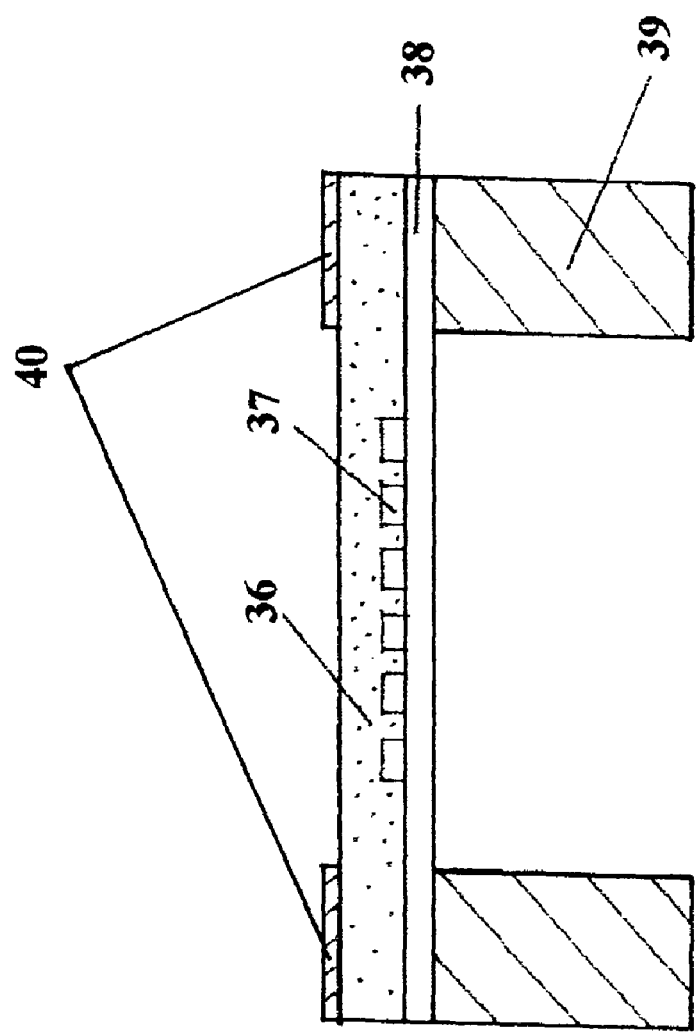
FIG. 6 depicts detail of the MEMS module used in a preferred embodiment of the present invention which is basically an all solid state micro hot plate fabricated on a thin micromachined membrane supported by a silicon cavity structure.

The MEMS module 4, as depicted in FIG. 1, is a wire bondable microelectronic device which acts as the source of infrared radiation for the presently invented NDIR gas sensor fuse as depicted in FIG. 6. Basically it is an all solid state micro hot plate fabricated on a thin micro-machined membrane. A high emissivity layer of black platinum film 36 is deposited onto a heater resistive structure 37 supported by a thin $Si_3N_4$ membrane 38 which is part of a silicon substrate cavity structure 39 as shown in detail in FIG. 6. When voltage is applied through wire bondable pads 40, heater resistive structure 37 gets hot very quickly and depending upon how much and how long voltage is applied to the device, heater resistive structure 37 acts like a near perfect blackbody source with emissivity approaching unity. As shown in FIG. 3, infrared radiation from MEMS module 4 is directed via the reflecting surfaces of the detector can housing 2 to detector modules 5 and 24 constituting, respectively, the Reference and Signal channels of the presently invented NDIR gas sensor fuse.

All voltages needed to drive the optoelectronic components mounted on detector header housing 1 are derived from a wire bondable voltage regulator die 41 (see FIG. 1). Voltage regulator die 41 is fed by an external voltage source via leads 35 of detector header housing 1. The output from the voltage regulator die 41 is first connected to CPU die 34 which then supplies the other optoelectronic components, viz. detector modules 5 and 24, MEMS module 4 and also a heater die 42 (see FIG. 1) which can be used to regulate the internal temperature of the space between detector header housing 1 and detector can housing 2. In addition to receiving power from the CPU die 34, heater die 42 is also directly controlled by CPU dies 34.

While the invention has been described herein with reference to a preferred embodiment, this embodiment has been presented by way of example only, and not to limit the scope of the invention. Additional embodiments thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions.

What is claimed is:

1. A Non-Dispersive Infrared ("NDIR") gas sensor for detecting the presence of a chosen gas in a sample chamber, comprising:
    a mechanical housing comprising:
        a can having a plurality of inner reflective surfaces; and
        a header housing affixed to the can having a top surface with a first window and a second window formed in the top surface and a bottom header, said bottom header comprising:
            a plurality of bottom header reflecting surfaces;
            a first mirror for reflecting radiation passing from the can through the first window toward a first bottom header reflecting surface of the plurality of bottom header reflecting surfaces;
            a second mirror for reflecting radiation passing from a last bottom header reflecting surface of the plurality of bottom header reflecting surfaces through the second window toward the can;
            wherein radiation is bounced off the plurality of bottom header reflecting surfaces so as to create a radiation path length that is substantially greater than the distance between the first and the second mirrors;
    a Microelectronic Mechanical System ("MEMS") source affixed to the top surface that emits radiation when power is applied to it;
    a reference detector that produces a reference output;
    a signal detector that produces a signal output; and
    a microprocessor that receives the reference output and the signal output;
    wherein each of the reference detector and the signal detector have an identical narrow band pass filter with the same Center Wavelength ("CWL"), Full Width Half Maximum (FWHM) and transmittance efficiency at the CWL; and
    wherein the reference detector and the signal detector are affixed to the top surface so that the plurality of inner reflective surfaces and the radiation path length create a signal channel path length detected by the signal detector that is greater than a reference channel path length detected by the reference detector.

2. The NDIR gas sensor of claim 1, wherein the housing header is sealed to the can so as to create a hermetically sealed environment containing the top surface.

3. The NDIR gas sensor of claim 2, wherein the chosen gas is methane.

4. The NDIR gas sensor of claim 1, wherein the housing header is comprised of a metal.

5. The NDIR gas sensor of claim 4, wherein the microprocessor is a wire-bondable Central Processing Unit ("CPU") die.

6. The NDIR gas sensor of claim 5, wherein the wire-bondable CPU die further comprises a temperature sensor.

7. The NDIR gas sensor of claim 6, further comprising an electrical heater die affixed to the top surface for supplying heat to regulate the temperature of the header housing.

8. The NDIR gas sensor of claim 7, further comprising a voltage regulator affixed to the top surface.

9. The NDIR gas sensor of claim 1, wherein each of the reference detector and the signal detector are further comprised of a thermopile detector with the identical narrow band pass filter mounted on its top and communicable with an Application Specific Integrated Circuit ("ASIC") such that infrared radiation received by the thermopile detector after passing through the identical narrow band pass filter is converted into a digital signal ready to be transmitted to the microprocessor.

10. The NDIR gas sensor of claim 1, wherein the signal channel path length is sufficiently greater than the reference channel path length so that the electronics can use an absorption bias between the signal output and the reference output to determine the chosen gas concentration in the sample chamber.

11. The NDIR gas sensor of claim 1, wherein the first window is comprised of a lens that renders radiation entering the bottom header substantially collimated.

12. The NDIR gas sensor of claim 11, wherein radiation is reflected ninety degrees off the first mirror toward the first bottom header reflecting surface and ninety degrees off the second mirror toward the can.

13. A Non-Dispersive Infrared ("NDIR") gas sensor for detecting the presence of a chosen gas in a sample chamber, comprising:
    a Central Processing Unit ("CPU");
    a first and a second Integrated Detector Filter ASIC module ("IDFA"), each of which is comprised of a thermopile detector with an identical narrow bandpass filter mounted on top and communicable with an Application Specific Integrated Circuit ("ASIC") such that infrared radiation received by the thermopile detector after passing through the identical narrow bandpass filter is converted into a digital signal ready to be transmitted to the CPU;
    a mechanical housing comprising:
        a can having a plurality of inner reflective surfaces; and
        a header housing affixed to the can having a top surface with a first window and a second window formed in the top surface and a bottom header, said bottom header comprising:
            a plurality of bottom header reflecting surfaces;
            a first mirror for reflecting radiation passing from the can through the first window toward a first bottom header reflecting surface of the plurality of bottom header reflecting surfaces;
            a second mirror for reflecting radiation passing from a last bottom header reflecting surface of the plurality of bottom header reflecting surfaces through the second window toward the can;

wherein radiation is bounced off the plurality of bottom header reflecting surfaces so as to create a radiation path length that is substantially greater than the distance between the first and the second mirrors; and a Microelectronic Mechanical System ("MEMS") source mounted to the top surface that emits radiation when power is applied to it;

wherein the first and the second IDFA are affixed to the top surface so that the plurality of inner reflective surfaces and the radiation path length create a signal channel path length detected by the first IDFA that is sufficiently greater than a reference channel path length detected by the second IDFA so that the CPU can use an absorption bias between a signal output of the first IDFA and a reference output of the second IDFA to determine the chosen gas concentration in the sample chamber.

14. The NDIR gas sensor of claim 13, wherein the housing header is sealed to the can so as to create a hermetically sealed environment containing the top surface.

15. The NDIR gas sensor of claim 14, wherein the chosen gas is methane.

16. The NDIR gas sensor of claim 15, further comprising an electrical heater die attached to the top surface for supplying heat to regulate the temperature of the header housing.

17. The NDIR gas sensor of claim 16, further comprising a voltage regulator affixed to the top surface.

18. The NDIR gas sensor of claim 17, wherein the CPU is a wire-bondable Central Processing Unit ("CPU") die.

19. The NDIR gas sensor of claim 18, wherein the wire-bondable CPU die further comprises a temperature sensor.

20. The NDIR gas sensor of claim 19, wherein radiation is reflected ninety degrees off the first mirror toward the first bottom header reflecting surface and ninety degrees off the second mirror toward the can.

* * * * *